(12) United States Patent
Bro

(10) Patent No.: US 6,249,809 B1
(45) Date of Patent: *Jun. 19, 2001

(54) AUTOMATED AND INTERACTIVE TELECOMMUNICATIONS SYSTEM

(76) Inventor: William L. Bro, 233 Wilshire Blvd., Suite 335, Santa Monica, CA (US) 90401

(*) Notice: Subject to any disclaimer, the term of this patent is extended or adjusted under 35 U.S.C. 154(b) by 0 days.

This patent is subject to a terminal disclaimer.

(21) Appl. No.: 09/034,271

(22) Filed: Mar. 4, 1998

Related U.S. Application Data

(63) Continuation-in-part of application No. 08/315,630, filed on Sep. 30, 1994, now Pat. No. 5,722,418, which is a continuation of application No. 08/112,955, filed on Aug. 30, 1993, now Pat. No. 5,377,258.

(51) Int. Cl.[7] .................................................. G06F 15/16
(52) U.S. Cl. ........................... 709/217; 379/38; 379/92; 379/93; 128/732; 600/545
(58) Field of Search ..................... 709/217; 600/545; 379/106.02, 92, 93, 38; 128/732

(56) References Cited

U.S. PATENT DOCUMENTS

| | | | |
|---|---|---|---|
| 5,377,258 | * 12/1994 | Bro | 379/106.02 |
| 5,596,994 | * 1/1997 | Bro | 600/545 |
| 5,633,910 | * 5/1997 | Cohen | 379/38 |
| 5,722,418 | * 3/1998 | Bro | 600/545 |

OTHER PUBLICATIONS

Electronic Communication With Patients (JAMA) Jul. 9, 1997 vol. 278, No. 2.

* cited by examiner

Primary Examiner—Mark H. Rinehart
Assistant Examiner—Paul Kang
(74) Attorney, Agent, or Firm—Sanford Astor

(57) ABSTRACT

An automated and interactive system that allows a physician, counselor, teacher, employer or trainer to produce and send information, messages and/or questions to, or to elicit responses or information from, a client, patient, employee or student. The system consists of a client database and a client program that includes for each client individual information. The database and program are operated by a central computer that has the capability to, at preselected or delayed time periods, send messages, information and/or questions to the client through the use of a variety of transmission means. The client is provided a message retrieval system having a visual indication that a message is waiting to be retrieved. The client's telecommunication system also has an automatic dialer, such as a one-button dialer, which will automatically connect the client to the central computer, to make it extremely simple for the client to communicate to the central computer via telecommunications to listen and interact with the message, information or questions. The message retrieval system may be connected through the client's telephone, television, computer or any other telecommunications system, and the message may be in an audio, video or text mode.

33 Claims, 3 Drawing Sheets

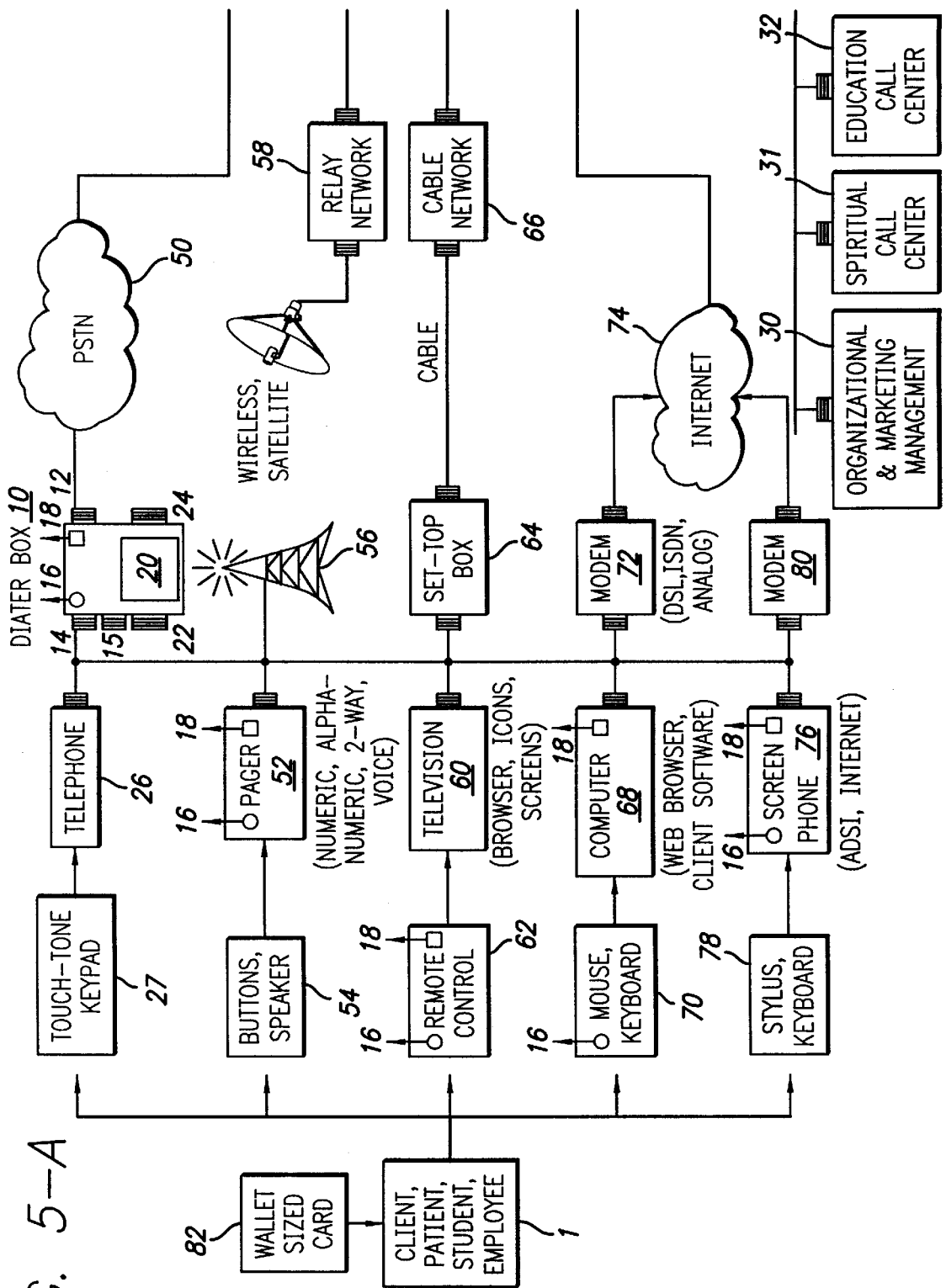
FIG. 5-A

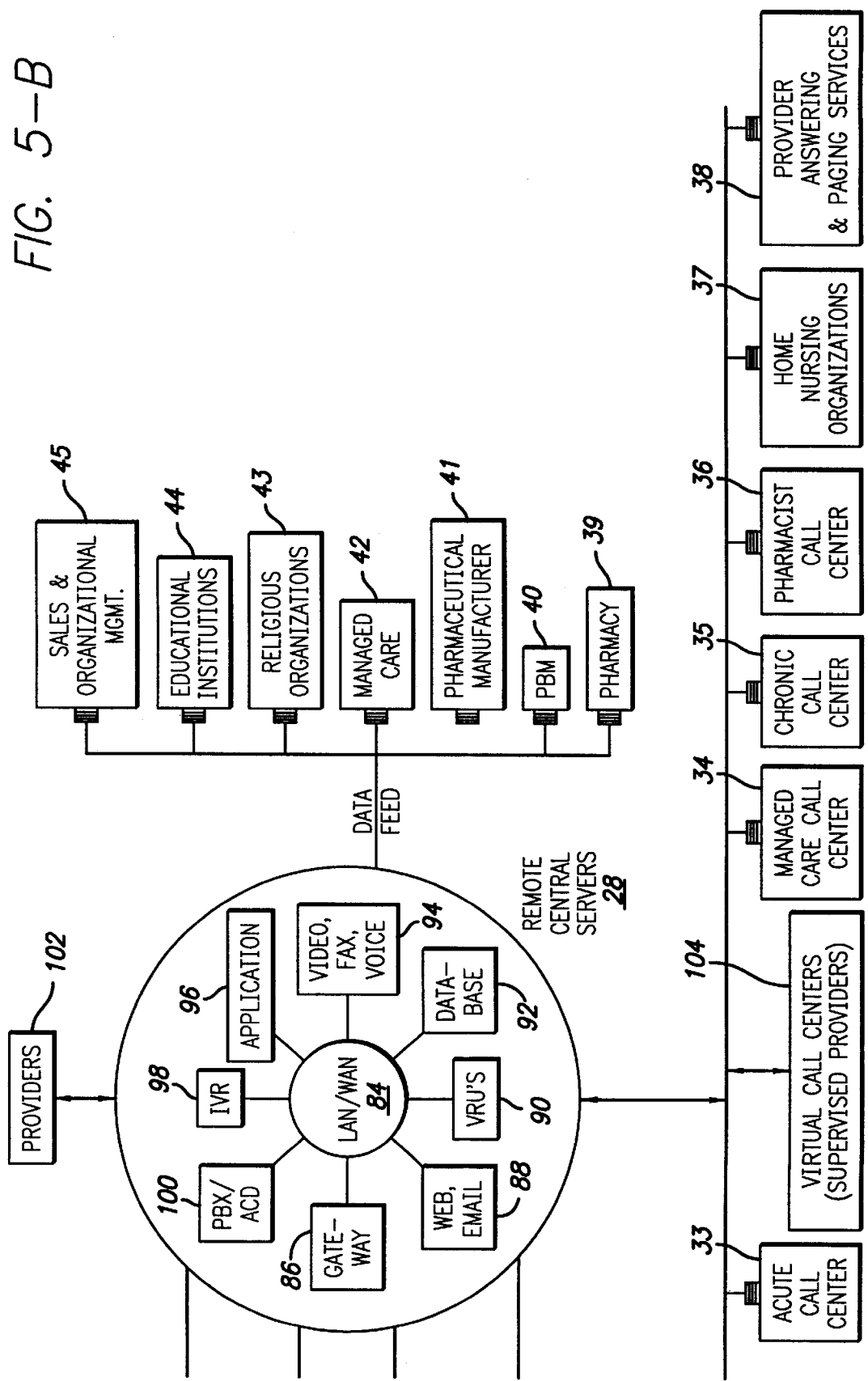

US 6,249,809 B1

AUTOMATED AND INTERACTIVE TELECOMMUNICATIONS SYSTEM

CROSS-REFERENCED RELATED APPLICATION

This application is a continuation-in-part of my previously filed application Ser. No. 08/315,630 filed Sep. 30, 1994 now U.S. Pat. No. 5,722,418.

TECHNICAL FIELD

The invention pertains to the general field of information exchange services, in business, education and personal health care and more particularly to a computerized telecommunication system that conveys information, such as health awareness and goal management messages, capable of maintaining guidance and surveillance over patients, employees, or students, generally called clients, by periodically sending health information, or other types of information, messages, and/or questions that require a client's interaction. In addition, the system uniquely utilizes social power through the avenue of telecommunications for modifying human behavior. It draws upon or is utilized by various authority figures or peers alternatively for modifying or reinforcing human behavior and for providing and eliciting information. The system can be supplemented by the addition of an expert or authority figure, such as a physician or administrator, to the system for providing interactive behavioral and motivational guidance to increase healthy behavioral changes to the client's prescribed medical regimens, educational or work goals, based upon the client's interaction over a period of time. Alternatively, peers or other persons of social influence may be added through the system to enhance each individual's performance.

BACKGROUND OF THE INVENTION

One of the major advances of present-day society is in the field of computer telephony and more particularly computerized telecommunications. Today, in the growing fields of healthcare, medical monitoring, quality control, pharmaceutical research, social psychology, behavioral medicine, and human motivation, formal verbal interchange is essential to provide modification of behavior along with its continuing reinforcement and ongoing information. In addition, measuring, monitoring and follow-up is essential to quality healthcare delivery. By using computerized telecommunications coupled with interactive voice response technology (IVR as it is known in the field of computer telephony), a client's, patient's or employee's behavior can be modified and reinforced at the site where behavior occurs and wherever the client, patient or employee goes. In addition, his or her medical condition can be continuously tracked.

It has been found that, as the frequency of reinforcing feedback increases, the client shows more rapid progress towards a particular goal. Similarly, the establishment of goals requires feedback and feedback requires goals, thus feedback is one of the key mechanisms in which goals are attained and the practice of medicine requires efficient and economical means for delivering healthcare. In medical practice, more frequent contact with the patient improves the quality and effectiveness of care.

However, numerous studies have shown that feedback in itself does not have the power to motivate performance without the establishment of goals. By utilizing a system of personalized and continuous computerized reinforcement, a client can be provided with more opportunity and greater frequency of economical therapeutic contact or feedback than through treatment or supervision in person. Additionally, the use of an interactive system vastly increases the therapeutic effect of this method of behavioral modification and reinforcement. As such, the subject invention uniquely mediates positive or beneficial expectancies of the physician, counselor, manager, administrator or other authority figure to the patient, student, client or employee. In addition, it builds a data base for monitoring client or patient populations.

Learning is enhanced through interactive feedback, and feedback heightens the learning experience. In traditional adult education, motivation, and behavioral modification, the amount of continuing feedback is limited to the time actually spent with a physician, counselor or supervisor, or in a class or seminar. Here, too, the feedback is limited to the actual time the physician, counselor, supervisor or trainer spends providing interaction with any one client, student or employee. By contrast, the addition of a computer and telecommunications or broadcast transmission allows "narrowcast" interaction and feedback on a continuous 24-hour basis to the client, student or employee wherever he or she goes, allowing for far greater frequency of interaction. Most importantly, in the case of adult behavior modification, this feedback, reinforcement, and resulting motivation becomes economically available for the first time at the site where the behavior occurs. Further, it permits a more economical means of providing measuring, monitoring and follow-up of patients, clients, students and employees.

As set forth in detail in my parent patent application Ser. No. 08/315630, a need exists for a computer driven interactive two-way communication link that increases the opportunity to create realistic and engaging behavioral reinforcement and guidance in the home or office and at remote locations, with both stationary and portable wired and wireless communication devices to assist the physician in the practice of medicine by facilitating compliance with medical requirements in regard to their patients. A need also exists for more effectively measuring, monitoring and providing follow-up of patient populations. Similarly, a parallel situation exists in business and educational organizations for the motivation of employees or students on a continuing basis in their natural environment.

The use of various telecommunication devices and computers, uniquely permits the greater personalization of medical treatment and education on a continuing basis.

A computerized interactive telecommunication system increases the client's, patient's, employee's or student's ability to resolve his medical, school or work problems at the site where his behavior occurs, and adjusts him within the framework of a preset goal. By including, within the context of the personalized message, challenges in the form of questions, an entertaining, rewarding and stimulating process can be added due to the increased feedback or interactive nature of new telecommunication technology.

With regard to the prior art, as set forth in my parent patent application Ser. No. 08/315,630, many types of systems have endeavored to provide an effective means for providing surveillance over the monitoring and behavioral modification of a patient or client by using a telecommunication link. However, these prior art systems have not disclosed an adequate and cost-effective telecommunication network that uses a remote computer in combination with a telephone or other platforms to provide positive behavioral, motivational and monitoring messages and/or questions that are answered by a patient, client, student or employee by means of a dual tone multifrequency telephone set or other telecommunication platforms, nor have adequate access methods or interfaces been provided.

OBJECTS OF THE INVENTION

It is an object of the present invention to provide a visual message-waiting indicator, icon or screen for a client connected to the system described.

Another object of the invention is to provide a one-button speed dialer, push button remote control or mouse, to be used in combination with a visual message-waiting indicator, to make the client's connecting to the system as simple as possible and to provide rapid connectivity through a telecommunications network to remote computer servers that direct inbound calls to live and realtime caregivers, teachers, employers or non-realtime recorded audio or video messages and information.

Yet another object of the invention is to provide video and audio messages or monitoring through a client's television set and television remote control device which access remote computer servers, as above.

Still another object of the invention is to provide audio and video messages or monitoring through a client's personal computer and mouse device which access remote computer servers through the telecommunications network, as above.

SUMMARY OF THE INVENTION

The automated and interactive system of this invention is designed to be used by doctors, managed care organizations, pharmacists, pharmacy benefit managers, pharmaceutical manufacturers, psychologists, counselors, teachers, managers, administrators, peers or other trainers to provide motivational and/or informational messages and/or questions to patients, employees, students, etc. (collectively referred to as clients) needing information, having behavioral, instructional, volitional or motivational problems or from whom responses to inquiries of any nature are required. Its basic configuration comprises:

(a) means for creating and retrieving a client database that includes for each client the name, schedule of telephone numbers where the client may be reached during each 24-hour period, personal identification number, client history and previous history of messages and the client's responses;

(b) means for creating and retrieving a client program that includes for each client, specific information, motivational messages, personal and unique metaphoric references, goals, and/or questions that are to be responded to by the client through the client's telecommunications interface such as the telephone, one- or two-way interactive beeper, personal communicator, modem, personal computer, or interactive television;

(c) a remote computer having means for retrieving the client database and said client program. If a match is found between a client database and client program, the computer produces in sequence, a digital telecommunications signal which corresponds to the client's telecommunications interface, a digital client validation request signal and digital information, motivational message(s) and/or question(s). The information, messages and/or questions are only then sent if the client's validation request signal is responded to by the client with a valid response signal;

(d) means for converting the digital signals produced by the computer to telecommunication signals that are sent to a client's telecommunications interface, such as a dual tone multifrequency telephone set, a hand-held wireless device, a television and digital set-top box or a computer and modem via a telecommunication network. The telephone set, television, wireless interface or computer is used by the client to respond to the remote computer's validation request, and to hear and/or see the information, messages and/or respond to the questions;

(e) means for converting the telecommunication signals originating at the client's telephone set, personal computer, television set-top box or hand-held wireless device, to digital signals for application to and processing by the remote computer;

(f) means for permanently recording all the outgoing and incoming client communications; and (g) visual or graphical message-waiting means associated with the client's telecommunications system.

The system may optionally also include automatic dialing means associated with the visual message-waiting means and/or interactive voice response means providing selection from a menu and sub-menu of choices, which activate a remote host server computer to interconnect a client, patient, student or employee to physician, pharmacist, nurse, manager or teacher who responds in a live or recorded manner.

Other optional additions to the system include, means for measuring and recording various medical tests including a patient's weight, blood pressure, glucose, etc., and transmitting the test results information via the telecommunication wire or wireless system, and/or a magnetic card reader which can store medical or other information which can be transmitted via the telecommunication system.

An important object of the invention is that the system manipulates speech or video messages that are stored, not in the analog format common to audio tape storage systems, but in digital format stored on a read-only compact disc, computer hard drive or other storage media. The use of storage media, such as a compact disc, allows the system to access files quickly and accurately and to access more than one speech or video file at a time. Each telecommunication line that the remote server system is servicing is actually a small "slice" of computer time during which audio or video files are being played from or recorded. The more lines that are active, the more slices of time that must be managed. The system provides the functions to operate with more than one telecommunication line simultaneously, thereby allowing a physician, pharmacist, manager, teacher or other counselor, at all times over a 24-hour period, to process and supervise many more client's, patients, employees and students than otherwise. In addition, the system allows for a client, to receive more frequent doses of information, queries, or behavioral intervention, over any time period, than in any other manner.

Another object of the invention is directed to accomplishing most tasks in a voice response application by accepting, recognizing and making decisions based on a keypad input from the caller's dual tone multifrequency telephone, computer, or remote control TV device. The telephone keypad generally sends dual tone multifrequency (DTMF) tone signals but occasionally multifrequency (MF) tones are used by certain types of telephone switching equipment. While these two signaling methods are not compatible, the system will work with either one equally well.

The improvement to Applicant's previously disclosed system includes a visual message-waiting indicator, visual icon, or screen interface (which may also have an audio signal therewith), associated with the client's telephone, television or personal computer. One of the biggest problems associated with any voice mail message system is the need of the user to call in to determine if messages have been left. By providing a visual message-waiting indicator or icon, the client will see a light or icon illuminated at his telephone or other telecommunication site, (with an associated audio signal if desired) so that he or she immediately knows that a message is waiting. Otherwise the client might go for long periods of time without checking his or her messages, thus delaying the information, message or questions which are to be delivered at a precise beneficial time.

The visual message-waiting indicator, icon or screen may have other beneficial features associated with it, which are described in detail in the following description of the drawings.

An additional optional feature of the subject invention is a push button connected to a dialer chip. When activated, the dialer connects the caller using the telecommunication device, first to voice mail to retrieve messages and then, by pushing a button, connecting him or her through a menu or sub-menu to the host or server computer through the connection to the telecommunications facility. The host or server computer can then provide a menu, and sub-menu when appropriate, of choices. The caller can use the DTMF keyboard on the telephone, the remote television control or computer mouse or keyboard, to select from the menu and in turn be interconnected to live or recorded counseling, information or queries. Alternatively the TV remote control can be used in conjuction with a digital set-top box to facilitate two-way telecommunications. Alternatively, the personal computer mouse or keyboard can be used in conjunction with the personal computer to facilitate connection to remote computers through the telecommunications network. For the purpose of the invention, the term "telecommunications network" shall include television cable, fiber-optic, satellite wireless, internet and various digital subscriber line (DSL) technologies.

There can also be provided means to access databases other than the host computer network, in order to integrate the system with existing databases, such as managed care systems, information systems, or best practice systems.

BRIEF DESCRIPTION OF THE DRAWINGS

The above stated objects will be shown in the accompanying drawings in which:

FIG. 5 is a schematic showing the interactive activity between the system and the client;

Figure 1:
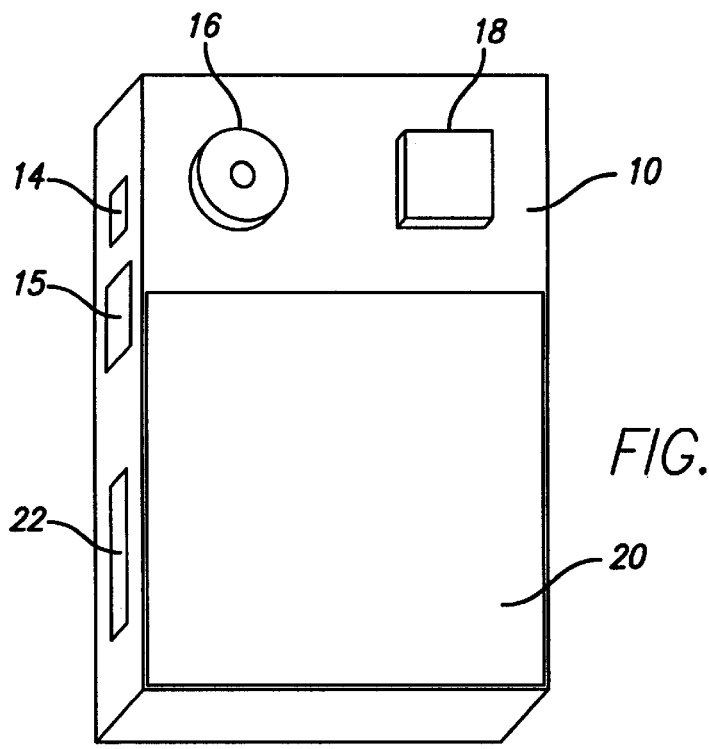
FIG. 1 is a perspective view of a stand alone visual message-waiting indicator base of this invention.
Figure 2:
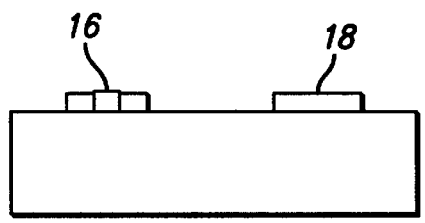
FIG. 2 is an end view of the indicator.
Figure 3:
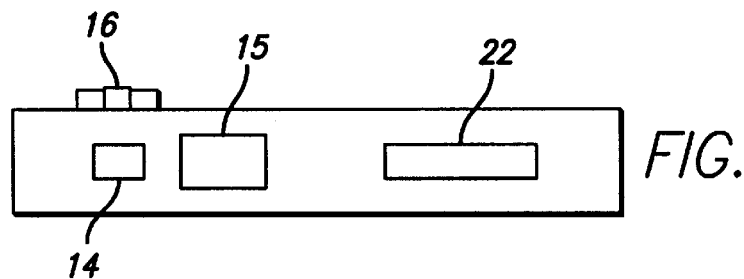
FIG. 3 is a left side view of the indicator.
Figure 4:
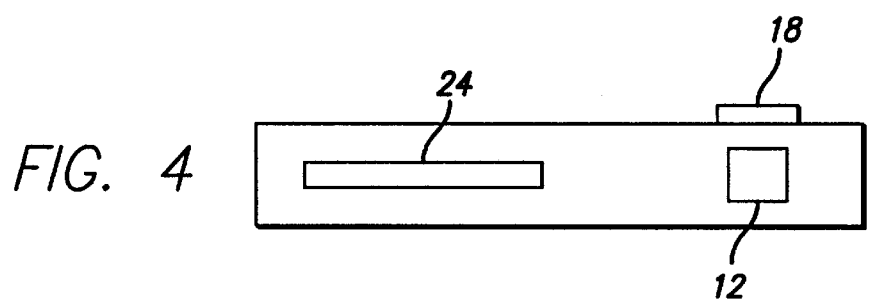
FIG. 4 is a right side view.

Referring now to the drawings there is shown a visual message indicator box 10. Box 10 is connected to a telephone line by plugging the telephone instrument line into receptacle 12 and plugging a line from receptacle 14 of box 10 into the telephone line receptacle. A light, such as a light emitting diode 16, lights or blinks when there is a message to be retrieved. Visual indicators of this simple type are well known, such as devices manufactured by Notify Corporation, Solo Point, Bejed, Inc., Ektel, Phone Labs Technology Company, Inc. SNI Innovation, Inc., etc.

Box 10 also has a programmable speed dial button 18 which is programmed to dial directly into the remote computer system, so that the client does not even have to look up the number to access the system for his motivational messages, questions or information. Once the remote computer is accessed, a menu of choices for interconnection to various services and information can be provided. An option if desired, is a note pad of paper 20 provided for the client to make notes as he sees fit.

Box 10 is optionally provided with one or more of the following additional features. There may be a standard interface socket 22 to connect to a monitoring device, such as a scale, blood glucose, blood pressure monitor or any other medical or television monitoring device. This would allow the client to have various important medical tests and visual observation done remotely and have the results or observations automatically transmitted remotely through telecommunications, to a central computer through box 10.

Box 10 may also be equipped with a universal smart card reader 24 which can be used to swipe a client's health benefit card, to have automatic transmission of a client's health care plan, insurance or other medical information. Box 10 may also contain complex memory or multi-processor chips which can process, store and direct information between the remote computer and a variety of counselors and institutions.

Box 10 optionally has a cable or network adaptor 15 for integrating and networking with set-top devices, household appliances, computers and can also be used in conjunction with cable networks.

Light 16 of box 10 may be equipped to provide intelligent beeps or colors, which indicate the urgency of callback, by the color or the frequency of the blinking light being of long or short duration.

Box 10 may also be equipped with automatic data upload/download capability which would allow for various information to be transmitted in either direction over the telecommunication line.

Box 10 may also be equipped with an infrared sensor to communicate with other devices which are reactive to infrared, for data collection.

The visual indicator, push button dialer concept of this invention may be extended far beyond its simple use with a telephone line. The device may be utilized from a phone line to a television set using internet or digital subscriber line (DSL) telephony. The push button there may utilize, or be a part of, a remote control device used to operate the client's television set containing the dialer and flashing light or an icon, internally or externally. That remote control device may have a one-button automatic dialer activator which accesses a dialer in a control box on the televison set, which connects the client directly to the remote central computer or server, as with the telephone system.

In addition, the television set may be used to deliver voice messages or visual messages or video clips, through internet or DSL telephony in addition to present cable systems. This expands dramatically the type and manner of messages that can be delivered to a client using Applicant's system. The message waiting indication may operate by flashing a message on the television set that a client has a call or E-mail message.

This is all made possible by the fact that many present television set-top boxes are individually addressable and accessable in both directions, since that is how pay-per-view systems operate. Newer digital set-top boxes manufactured by General Instruments and Scientific-Atlantic have a feature for video-conferencing and internet access. The client may listen, and interact with his messages, through the television, through his telephone, coaxial cable, wireless, satellite or any other means of telecommunications. The effectiveness of Applicant's motivational message and informational system is enormously enhanced by its ability to notify the client visually that a message is waiting, and should be retrieved by its ability to deliver that message over telephone, personal computer and/or television. The dialer button greatly enhances immediate connectivity.

The television remote control or set-top control box may be equipped with the same monitoring connectors and universal smart card reader as previously described.

Referring now to FIG. 5, there is shown the client 1, and the client's telephone 26 with its touch-tone keypad 27 connected through visual indicator/dialer box 10. The one-button dialer 18 will connect the client through a PSTN (Public Switched Telephone Network) line 50 to the system remote computers or servers 28.

Similarly, a pager 52 with its buttons and speaker 54 and having visual indicator 16 and one-button dialer 18, will connect the client through wireless transmitter 56 and satellite relay network 58.

A client's television set 60 with its remote control device 62 having the visual indicator 16 and one-button dialer 18 will connect the client through the set-top box 64 through a cable network 66.

A client's computer 68 having an icon automatic dialer 18 and a mouse and keyboard 70 having visual indicator 16, will connect the client through modem 72 through the internet 74.

Similarly, a screen phone 76 having visual indicator 16 and one-button dialer 18, and having a stylus, touchscreen or keyboard 78, will connect the client through modem 80 and the internet 74.

Central network computer servers 28 comprise a gateway 86, E-mail and web server 88, voice response units 90, database 92, video, voice and fax servers 94, application servers 96, interactive voice response system 98 and PBX/ACD unit 100, connected in a LAN/WAN 84 configuration.

Providers 102 dial into or connect to the remote central servers 28, to access client, patient, student or employee information and provide information and/or messages by setting up interactive or informational calls. The providers in a virtual call center 104 environment can access the remote servers 28 through the live call centers 30–38 so that the calls and messages created can be supervised or monitored by supervisory staff at the call centers.

To illustrate its functions, as an example for medical care, through a touch tone system, icons or screens or through automatically programmed directions, the client, for example, can be connected to such providers as, organization and marketing management call center 30, spiritual call center 31, educational call center 32, acute care call center 33, managed care call center 34, chronic care call center 35, pharmacy call center 36, home nursing organization 37 or physician or other medical care provider answering or paging service 38. Each of these call centers is accessed through an individual computer server, which is remotely located, as previously described in my parent patent application.

The remote computer servers would have the capability to connect to third party databases for data feed and information exchange, which could consist for example, of pharmacy 39, pharmacy benefit manager (PBM) 40, pharmaceutical manufacturer 41, managed care 42, religious organizations 43, educational institutions 44 and sales and organizational management 45.

The following represent additional or preferred features which can be used in conjunction with the subject invention:
1. A wallet-sized card 82 containing the telephone number of the patient, employee, client or student's voice mail box;
2. A wallet-sized card 82 containing the above with the addition of a computer chip which can store medical or other information;
3. A wallet-sized card 82 containing any of the above and a magnetic-strip which can be read for identification purposes by a magnetic card reader;
4. A plurality of remote computers in diverse locations which may act from time to time as servers storing information and messages;
5. A plurality of remote computers which provide a menu and sub-menu of choices which can be activated remotely through telecommunications. Said computers acting on said choice initiation would then interconnect the caller to a variety of live operator or recorded messages;
6. Voice recognition and speech synthesis; and
7. Among the service menu choices to which the remote server could interconnect the caller are such service features as:
   (a) Fax on Demand—allows callers to request via touch tone a faxed back, printed copy of tests results, the physician's, pharmacist's, or nurse's instructions, or audio or video information they have listened to or watched, or a custom message file.
   (b) Feedback to Provider or Managed Care Organizations—provides an organized system for recording, categorizing and responding to customer complaints and issues. In addition, it tracks the resolution of the complaint or issues over time.
   (c) New and Continuing Member Information—provides information on the managed care organization services to new and continuing members.
   (d) Paging System Interface—allows the patient/member to quickly page or transmit a message to his or her physician, or other healthcare provider, by directly calling the physician's specified paging service.
   (e) Parent Advice—provides live counselor or nurse and/or recorded advice in order to permit parents and caregivers to make informed decisions on the routine care of children.
   (f) Patient and Member Assessment Tests—the tests are designed to ask questions of patients and members of managed care organizations to identify potential risks early and to help educate patients and members in disease prevention and management of their own health. Other assessment surveys include patient satisfaction and medical care quality surveys such as national HEDIS quality surveys and those used to detect errors in practice and compliance with clinical guidelines.
   (g) Health Information Library—providing information on hundreds of general health topics to educate patients and members.
   (h) Health News Flashes—audio or video abstracts of recent published medical findings from authoritative medical journals. When used in conjunction with a live nurse or other healthcare provider, topics can be discussed with callers over the phone, printed and mailed, or faxed as necessary.
   (i) Pin Identification and Verification—permits direct input of a Personal Identification Number (PIN) prior to access of features restricted to classes of members or patients. Among these applications would be the use of this feature for secure retrieval of patient test results.

(j) Patient Test Results—provides patient test results and physician or other provider follow-up instructions. A physician or staff member can record test results and follow-up instructions using individual audio or video messages in the patient or member's audio or video "mail box," which each patient can access via touch tone telephone, a personal computer, or a television set-top box and remote control. In the case of positive results, the patient can be provided with DTMF push button Interactive Voice Response (IVR) or push button remote access in conjunction with the TV set-top box direct access routing to the physician or his staff. The benefits of such a feature eliminates multiple calls to patients, premature calls to the physician's office by various patients, and unrelated conversation that frequently occurs when either physician or staff speak with patients directly.

(k) Provider Referral—connects patients and members to live operator or recorded referrals to local healthcare professionals. Callers can be matched according to criteria found in patient or member medical records for best match. Optometrists, pharmacists, psychotherapists, dentists, chiropractors, acupuncturists, and various alternative medical providers can be accessed through this feature. Another variation is for its use between physicians or between physicians and pharmacists or other medical specialists.

(l) Patient Appointment Reminders—a recorded message reminding the patient of his appointment with the medical provider or for home health visits. The patient can always access this message, however, another feature would be to have the message timed to call him and play the recording the day before the appointment. No shows would receive calls and recorded reminders to re-schedule their missed appointments.

(m) Service Authorization—use of this feature would request authorization of medical services and/or referral to providers. It would list plan coverage and would retrieve a unique authorization number which would be assigned when referrals are made. It also would enroll member registrants into classes or screenings and be used in conjunction with the administration and tracking of patient compliance protocols and physician compliance with practice guidelines. It could also be available to providers for use in the authorization of medical procedures.

(n) Specialty Call Centers—direct connection to live or recorded counseling and information in medical call centers with specialists working with members and patients with issues such as, pediatric, geriatric, chronic disease, behavioral or women's health counseling.

(o) Directions to Facility, Staff and Mailing Address— directions to facility adjusted by zip code of caller, fax, or demand maps. Information on individual physicians as to age, education background, years in community, and professional affiliations. Automatic transfer feature connecting callers to appropriate department or care center.

(p) Call Back Request—allows patient or member to leave message for provider. Optional feature is to have patient receive an estimate as to time that will elapse before a call or message will be received.

(q) E-Mail Reader—users are able to access electronic mail which resides in an E-Mail box. Using text-to-speech software and voice synthesis, text base messages in HTML or otherwise are read over the telephone to the user of the subject device.

(r) Automatic Voice Response—a feature which permits the patient, employee or student to record a message which can be played as a personal message, greeting, or explanation for non-reply, such as, "I'll be back next week".

(s) Refill reminders—a refill request could be entered using the system. Callers could be transferred to a pharmacist's phone at anytime during the call. The pharmacist would be provided with screens showing calls, orders and voice messages through a personal computer. The remote server could also provide daily and periodic statistical reports and summaries.

(t) Create a personal directory for the menu and sub-menus, using caller ID, which builds and up-dates the new menu from past calls.

(u) Claims Information—for use by members and providers in tracking the progress of a claim in the payment process.

(v) Plurality of remote computers in diverse locations which, when accessed, provide icons or entire screens of choices and options to the user's television screen, personal computer or screen phone.

8. A wallet-sized plastic or paper card containing the telephone number of the client, patient, employee or student's voice mail box number or I.D. number, to be used by a third party provider, such as a pharmacist, administrator, etc., to provide pharmaceutical products, over-the-counter healthcare products, consumer medical appliances, products or services to the client.

9. A wallet-sized plastic or paper card containing the telephone number of the client, patient, employee or student's voice mail box number or I.D. number, to be used in combination with an on-line browser, network, or operating system.

10. An icon or screen on the television or screen interface of the client, patient, employee or student to be used in combination with on-line or television services.

11. The ability of the Client's telecommunication system to to be used to access, on-line magazines, systems and browsers.

12. The ability to download audio and/or video data to a client's telecommunications system in non real-time, which would provide information, messages and/or questions with which the client would interact when he or she accessed the system. All interaction by the client would be uploaded to the central computer for processing.

Having thus described the invention, I claim:

1. An automated and interactive informational system comprising:

a) means for creating and retrieving a client database;

b) means for creating and retrieving a client program that includes for each client either specific messages, information or questions;

c) computer means for accessing said client database and said client program, said computer producing in sequence, a telecommunication address, a digital client validation request signal and one of either a digital message, question or information that are only sent if the client validation request signal is responded to by the client with a valid response signal;

d) means for converting the digital signals produced by said computer to telecommunication signals that are sent to a client's telecommunications interface in response to the client's validation response signal;

e) means for converting the telecommunication signals originating at the client's telecommunications interface, to digital signals for application and processing by said computer;

f) means comprising a light ar illuminated icon associated with said client's telecommunications interface to visually indicate that a message is waiting or information is available.

2. The system of claim 1 further comprising means associated with the client telecommunication interface to automatically access said computer.

3. The system of claim 2 in which said means to automatically access said computer is a one-button dialer.

4. The system of claim 1 further comprising means for recording all outgoing and incoming client communications.

5. The system of claim 1 further comprising interactive voice response means providing selection from a menu of choices, which activate a remote host server computer to interconnect said client to either of a physician, nurse, manager or teacher who responds in live or recorded manner.

6. The system of claim 1 further comprising means to access databases other than said remote computer.

7. The system of claim 1 further comprising an audio message-waiting signal in addition to the visual signal.

8. The system of claim 1 further comprising interface means for monitoring of medical conditions.

9. The system of claim 1 further comprising a smart card reader associated with said message-waiting means.

10. The system of claim 1 further comprising processor means, associated with said message-waiting means, for storage and processing information.

11. The system of claim 1 further comprising automatic upload/download means for transmitting information in either direction.

12. The system of claim 1 further comprising infrared sensor means, associated with said message-waiting means, for communication with infrared sensor devices.

13. The system of claim 2 in which said automatic dialing means comprises a one-button dialer connected to a telephone line, television remote control device, mouse or television set-top box.

14. The system of claim 1 in which said message-waiting means is a visual message on the client's television set or an E-mail message on the client's computer.

15. The system of claim 1 in which said message-waiting means is a visual indicator on the client's telephone, one-button dialer, television remote control, television set-top box, television screen, or screen-telephone screen.

16. The system of claim 1 further comprising voice recognition means.

17. The system of claim 1 further comprising paging means to notify the client of a message waiting.

18. The system of claim 1 further comprising means for video monitoring of said client.

19. The system of claim 2 in which said means to automatically access said remote computer is an icon on the personal computer, television or screen-phone screen interface.

20. The system of claim 1 further comprising means to provide the visual message-waiting indicator with intelligent beeps or colors to indicate the urgency of the message.

21. The system of claim 1 further comprising means to connect the client to a live operator.

22. The system of claim 1 further comprising means for the client to record a message.

23. The system of claim 1 further comprising means for the client to use a wallet-sized card containing an identification number and a personal voice-mail telephone number, E-mail or web site address.

24. An automated and interactive informational system comprising:

a) means for creating and retrieving a client database;

b) means for creating and retrieving a client program that includes for each client either specific messages, information or questions;

c) computer means for accessing said client database and said client program, said computer producing in sequence, a telecommunication address, a digital client validation request signal and one of either a digital message, question or information that are only sent if the client validation request signal is responded to by the client with a valid response signal;

d) means for converting the digital signals produced by said computer to telecommunication signals that are sent to a client's telecommunications interface in response to the client's validation response signal;

e) means for converting the telecommunication signals originating at the client's telecommunications interface, to digital signals for application and processing by said computer;

f) means comprising a light or illuminated icon associated with said client's telecommunications interface to visually indicate that a message is waiting or information is available;

g) means associated with the client telecommunications interface to automatically access said computer.

25. The system of claim 24 further comprising means for the client to use a wallet-sized card containing an identification number and a personal voice-mail telephone number, E-mail or web site address.

26. The system of claim 24 in which said means to automatically access said computer is a one-button dialer.

27. The system of claim 24 further comprising an audio message-waiting signal in addition to the visual signal.

28. The system of claim 26 in which said one-button dialer is connected to a telephone line, television remote control device, mouse or television set-top box.

29. The system of claim 24 in which said message-waiting means is a visual message on the client's television set or an E-mail message on the client's computer.

30. The system of claim 24 in which said message-waiting means is a visual indicator on the client's telephone, one-button dialer, television remote control, television set-top box, television screen, or screen-telephone screen.

31. The system of claim 24 in which said means to automatically access said remote computer is an icon on the personal computer, television or screen-phone screen interface.

32. The system of claim 24 in which the client's telecommunications interface provides access to on-line magazines, services and browsers.

33. The system of claim 24 further comprising means to automatically download information, messages or questions, in non real-time, to a client's telecommunications system.

\* \* \* \* \*